US008178121B2

(12) United States Patent
Nguyen-Xuan

(10) Patent No.: US 8,178,121 B2
(45) Date of Patent: May 15, 2012

(54) READY-TO-USE PARACETAMOL INJECTION SOLUTIONS CONTAINING PROPYLENE GLYCOL AS THE ONLY COSOLVENT

(75) Inventor: Tho Nguyen-Xuan, Vich (CH)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1508 days.

(21) Appl. No.: 10/492,648

(22) PCT Filed: Oct. 15, 2002

(86) PCT No.: PCT/EP02/11498
§ 371 (c)(1),
(2), (4) Date: Apr. 14, 2004

(87) PCT Pub. No.: WO03/033026
PCT Pub. Date: Apr. 24, 2003

(65) Prior Publication Data
US 2004/0247627 A1 Dec. 9, 2004

(30) Foreign Application Priority Data
Oct. 16, 2001 (IT) .............................. MI2001A2135

(51) Int. Cl.
| | |
|---|---|
| A61F 13/00 | (2006.01) |
| A01N 37/18 | (2006.01) |
| A61K 31/165 | (2006.01) |
| C07C 209/00 | (2006.01) |
| C07C 233/00 | (2006.01) |
| C07C 237/00 | (2006.01) |
| C07C 239/00 | (2006.01) |
| C07C 235/00 | (2006.01) |

(52) U.S. Cl. ................ 424/422; 514/617; 564/2; 564/4; 564/5; 564/6; 564/7; 564/223

(58) Field of Classification Search .................. 424/422; 514/617; 564/2, 4, 5, 6, 7, 223
See application file for complete search history.

(56) References Cited

U.S. PATENT DOCUMENTS 6,006,659 A * 12/1999 Rosenthal ........................ 99/451
6,028,222 A *  2/2000 Dietlin et al. ..................... 564/4

FOREIGN PATENT DOCUMENTS

| JP | 07250752 | 3/1997 |
|---|---|---|
| KR | 9311994 B | 12/1993 |
| WO | 8504106 | 9/1985 |
| WO | WO 98/05314 A1 | 2/1998 |
| WO | WO 98/06436 A2 | 2/1998 |
| WO | WO 00/07588 A1 | 2/2000 |
| WO | 01 93830 | 12/2001 |
| WO | 02/072080 | 9/2002 |

OTHER PUBLICATIONS

Krsteska Ljiljana et al., Increasing solubility and masking the unpleasant taste of paracetamol in oral pharmaceutical formultaion, ACTA Pharmaceutice (ZAGREB), 46(4): 329-332, 1996.
Yan Z, Fan Q, Preparation of paracetamol injections, STN Chemical Abstracts, vol. 105, Abstract No. 232386, Columbus, Ohio, US WP002125073 and English Abstract.
Notice of opposition against EP 1592414—corresponding Application No. EP04711333.7—grant date Apr. 21, 2010.
Notice of Opposition against EP 1592414 B1—corresponding Application No. EP04711333.7 dated Jan. 12, 2011.
Notice of Opposition against EP 1 592 414 B1—corresponding Application No. EP04711333.7 dated Jan. 21, 2011.
Notice of Opposition against EP 1 592 414—corresponding Application No. EP04711333.7 dated Jan. 19, 2011.
Notice of Opposition against EP 1 592 414 B1—corresponding Application No. EP047111333.7 dated Jan. 20, 2011.
Notice of Opposition against EP 1 592 414 B1—corresponding Application No. EP047111333.7 dated Jan. 14, 2011.
Record from Newport database for injectable paracetamol specifically indicating a launch date of Feb. 28, 2002 for Perfalgan—4 pages.
Fairbrother, "Acetaminophen" Analytical processes of Drug Substances, vol. 3, 1974—pp. 2-29.
Koshy et al., "Stability of Aqueous Solutions of N-Acetyl-p-aminophenol" Journal of Pharmaceutical Sciences, vol. 50, No. 2 (Feb. 1961), pp. 113-118.
Mahler et al. "Biological Chemistry" Harper & Row, 1971—6 pages.
Colowick et al., "Methods in Enzymology" Academic Press, Inc., vol. 1, 1955—cover pp. 1-2, pp. 138-145.
Handbook of Chemistry & Physics, 65th Ed., CRC, 1984, p. D-167—2 pages.
Merck Index, Twelfth Edition, 1996 monograph No. 9—3 pages.
Potter et al., "Identification of Acetaminophen Polymerization Products Catalyzed by Horseradish Peroxidase," The Journal of Biological Chemistry, vol. 260, No. 22, 1985—pp. 12174-12180.
Fischer et al., "Free-Radical Metabolites of Acetaminophen and a Dimethylated Derivative," Environmental Health Perspectives, vol. 64, pp. 127-137, 1985—pp. 127-137.
Greenwood et al., Chemie der Elemente, 1st Edition, 1990, VCH, Weinheim—p. 665.
Vilchez et al., "Spectrofluorimetric determination of paracetamol in pharmaceuticals and biological fluids," Journal of Pharmaceutical and Biomedical Analysis, vol. 13, 1995—pp. 1119-1125.
Potter et al., "Reactions of N-Acetyl-p-benzoquinone Imine with Reduced Glutathione, Acetaminophen, and NADPH," Molecular Pharmacology, vol. 30, 1986—pp. 33-41.
Clegg et al., "An Oxidatively Coupled Dimer of Paracetamol," Acta Crystallographica Section C, vol. 12 C54, 1998, pp. 1881-1882.
Remington's Pharmaceutical Sciences, 19th Edition, 1995—cover pp. 1-2, p. 1463.

* cited by examiner

*Primary Examiner* — Johann Richter
*Assistant Examiner* — Luke Karpinski
(74) *Attorney, Agent, or Firm* — K&L Gates LLP

(57) ABSTRACT

The present invention refers to ready-to-use highly stable paracetamol injectable solutions, prepared by mixing paracetamol, water, propylene glycol, and a citrate buffer. (pH 4.5 to 6.5), and by heating said solution under preset conditions. The resulting solution may be stored for an extended period of time within a wide range of temperatures, with no paracetamol precipitation and/or its chemical modification.

10 Claims, No Drawings

READY-TO-USE PARACETAMOL INJECTION SOLUTIONS CONTAINING PROPYLENE GLYCOL AS THE ONLY COSOLVENT

FIELD OF THE INVENTION

The present invention refers to liquid formulations for pharmaceutical use and in particular to the preparation of paracetamol solutions suitable for administration by injection.

Ready-to-use highly stable paracetamol injectable solutions are described herein.

PRIOR ART

Paracetamol (p-acetylaminophenol) is a broad-spectrum anti-inflammatory drug, well tolerated by man. Therefore, this drug may be especially used as an analgesic and antipyretic by the sick, young children and the elderly, and as a pain reliever in chronic therapies.

Paracetamol can be easily formulated as tablets or other solid forms, whereas some difficulties arise in the preparation of solutions, since paracetamol is scarcely soluble in water. Furthermore, in the presence of water and/or on exposure to light, paracetamol tends to hydrolyse to p-aminophenol. On its turn, p-aminophenol tends to form oxidation products (e.g. quinine imines), which impart a characteristic more or less intense pink colour to the solutions. By raising the temperature, the rate of paracetamol degradation increases, whereas by lowering the temperature, the solubility decreases with partial product precipitation and solution clouding. It follows that the paracetamol solution keeps optimal stability and solubility characteristics within a very narrow range of temperatures and that the storage of said solutions, especially in the cold, is extremely problematic. In fact, paracetamol tends to precipitate from its aqueous solutions already at temperatures of approx. 5° C., which temperatures are easily reached when the product is transported and stored in winter. Said limitations cause a real hindrance to chronic hospital treatments, which require ready-to-use perfusion solutions, perfectly stable in terms of product activity and perfectly dissolved.

Some authors tried to solve said problems by adding water to paracetamol immediately prior to use. For example, patent application WO 0007588 describes paracetamol solutions in wholly anhydrous polyethylene glycol; however, said solutions are not ready-to-use, but must be reconstituted just prior to injection, by adding a given quantity of water. This sets a limit to the practical use of the product. Other authors, e.g. in WO 9805314, tried to obtain ready-to-use solutions by the use of aqueous solutions in the presence of co-solvents mixtures. However, in said solutions, the product stability requires the presence of free radicals scavengers, and all traces of oxygen and other oxidants are removed by water insufflated with inert gases. Furthermore, said solutions cannot be stored in plastic containers as they can partially absorb oxygen from the atmosphere, to the detriment of the stability of the product contained in the solution. The fact that oxygen-labile compounds can be hardly stored in plastic containers makes it particularly difficult to prepare paracetamol formulations keeping stable in infusion bags.

Up to now there is no ready-to-use paracetamol injectable solution, stable within a wide range of temperatures, not undergoing product precipitation and/or degradation, and storable in oxygen-permeable containers.

SUMMARY

The present invention refers to ready-to-use paracetamol injectable solutions. Said solutions are prepared by mixing paracetamol, water, propylene glycol, and a citrate buffer (pH from 4.5 to 6.5), and by heating said solution under preset conditions. The resulting solution may be stored for a long time within a wide range of temperatures with no paracetamol precipitation and/or its chemical alteration.

DETAILED DESCRIPTION OF THE INVENTION

It is an object of the present invention to provide highly stable paracetamol injectable solutions obtainable by:
mixing paracetamol with water, propylene glycol, and a citrate buffer (pH from 4.5 to 6.5), and
heating the solution from 70° C. to 130° C. and keeping same at said temperature for 10 min at least.

In the preparation of the solutions according to the invention, the order of components mixing is not determining. For example, paracetamol suspensions may be prepared in buffered water and then added with glycol, or paracetamol may be dissolved in glycol and then added with buffered water, or paracetamol may be dissolved in a buffered water/glycol mixture prepared beforehand. Water and buffer can also be added separately.

Paracetamol is preferably used in a concentration up to 4% w/v (% g/100 ml).

Propylene glycol is preferably used in concentrations ranging from 0.1% to 40% w/v, more preferably from 0.5% to 20% w/v, and still more preferably from 0.5% to 10% w/v or from 0.7% to 3% w/v.

Propylene glycol concentrations higher than 40% w/v can be also used, if so desired.

All concentrations referred to hereinafter were calculated in respect of the final solution volume.

The presence of a citrate buffer, associated with propylene glycol, is essential for obtaining the high stability that characterises the solutions of the present invention. By citrate buffer is meant any chemical system allowing the co-existence in equilibrium of citric acid and one or more salts thereof, at a pH value in the range from 4.5 to 6.5, preferably from 5 to 6. An example of said systems is a buffer based on citric acid and disodium hydrogen phosphate. The concentrations of disodium hydrogen phosphate and citric acid preferably range from 0.08 to 1 w/v and, respectively, from 0.04 to 0.5 w/v.

The water used is sterile water for pharmaceutical use. According to the present invention there is no need for eliminating the oxygen dissolved in water or in the solutions thereof; deoxidising and/or preservative treatments may be optionally applied.

Heating is indispensable to secure product stabilisation. The solution heating time is at least 10 min, preferably at least 15 min. By heating time is meant the time during which the solution is kept in the indicated range of temperatures, i.e. excluding the time required to reach said temperature. According to the present invention, any heating system suitable for solutions heating may be adopted, e.g. heating jackets or bain-marie or solution exposure to a heated environment, etc. The heat can be applied to the solution containing water, glycol, and paracetamol or to the solution during its preparation, i.e. using preheated water and/or glycol. In any case, it is essential to maintain the final solution containing paracetamol at the indicated temperature for the time mentioned above.

A group of particularly preferred solutions contains paracetamol (1% to 2% w/v), propylene glycol (0.7% to 3% w/v), a citrate buffer (pH from 5 to 6); a solution of said group is kept at a temperature from 80° C. to 120° C. for at least 15 min.

To reach the required isotonicity to become suitable for injection, the solutions of the present invention preferably contain adequate quantities of salts, e.g. sodium chloride.

The present invention also includes the use of the solutions described so far in the preparation of highly stable liquid pharmaceutical compositions of paracetamol, suitable for injection or perfusion. Depending on the way of administration, the liquid pharmaceutical compositions of the present invention are filled into containers, e.g. injection phials or bottles or perfusion bags.

Although the present invention is particularly applicable to the preparation of solutions for injection and perfusion, it is not intended to be utilised in said applications only. In fact, it can be advantageously used to provide stable paracetamol solutions for administrations other than injection, i.e. by the oral way. It is thus possible to prepare oral solutions, syrups, topical washings, etc.

It is a further object of the present invention to provide a process for the production of the solutions described so far. This process consists in mixing paracetamol with water, propylene glycol, and a citrate buffer (pH 4.5 to 6.5), in heating said solution to 70° C.-130° C. and keeping same at said temperature for 10 min at least. As concerns the claimed process, the preferred conditions, in terms of concentrations of the single ingredients, buffers, and heating systems, are as already illustrated in the description referred to the solutions.

According to a preferred embodiment of the invention, a propylene glycol aqueous solution is prepared, heated to 40° C. at least, added, under stirring, with paracetamol, a citrate buffer (e.g. citric acid/disodium phosphate), isotonic agents (e.g. sodium chloride or glucose), if any, until complete dissolution, finally heated to 70° C.-130° C., and kept at said temperature for 10 min at least.

According to the present invention it is also possible to obtain ready-to-use stable solutions, without resorting to preservatives and scavengers; furthermore, water removal from the formulation is not required. The stability is secured also in partially oxygen-permeable containers, such as infusion bags. The high stability values, brought about by the invention, are obtained by the use of propylene glycol as the only co-solvent, i.e. the preparation of co-solvent mixtures is not required. High stability values can be also obtained with minimum co-solvent concentrations, e.g. 1%.

The paracetamol aqueous solutions according to the invention exhibit a high stability (no degradation and no precipitation) within a wide range of temperatures, i.e. at low and high temperatures. The stability in the cold is particularly useful in view of the compositions long-term storage in cold environments. In particular, the solutions can be stored for an extended period of time, e.g. 3 months or over, at a temperature of 2° C. to 8° C., e.g. 5° C., without any paracetamol precipitation and/or degradation. Heat stability is particularly useful for the preparation of commercial-scale lots.

The following examples are conveyed by way of indication, not of limitation, of the present invention.

EXPERIMENTAL PART

Cold Stability Tests

EXAMPLE 1

A solution consisting of paracetamol (1%), ethylene glycol (1%), monohydrated citric acid (0.047%), disodium hydrogen phosphate (0.089%), NaCl (0.4%), water to 100 ml was prepared, heated to 120° C. and kept at said temperature for 20 min. The solution, kept at 5° C. for 10 days, was perfectly stable; no recrystallisation occurred.

EXAMPLE 2

Three paracetamol solutions were obtained according to the present invention. The solutions characteristics are recapitulated in the following table. Values are expressed as % w/v.

| Composition | A | B | C |
|---|---|---|---|
| Paracetamol | 1.0 | 2.0 | 4.0 |
| Propylene glycol | 1.0 | 15.0 | 40.0 |
| Monohydrated citric acid | 0.045 | 0.091 | 0.182 |
| Disodium hydrogen phosphate.2 $H_2O$ | 0.091 | 0.182 | 0.364 |
| Injection water | to 100 ml | to 100 ml | to 100 ml |
| Heating time | 20 min | 20 min | 20 min |
| Heating temperature | 120° C. | 120° C. | 120° C. |
| Recrystallisation | no | no | no |

Solutions A, B, C, kept at 5° C. for 10 days, were perfectly stable; no recrystallisation occurred.

Heat Stability Tests

EXAMPLE 3

Solutions B and C as per Example 2 were stored at 25° C. or at 40° C. for 3 months in polypropylene infusion bags.

The 3-month paracetamol loss was evaluated in respect of the initial paracetamol quantity (100%).

| Test: | B (2% paracetamol) | | C (4% paracetamol) | |
|---|---|---|---|---|
| Temperature | 25° C. | 40° C. | 25° C. | 40° C. |
| Initial quantity | 100.8 | 100.8 | 100.1 | 100.1 |
| After 3 months | 100.6 | 99.2 | 99.7 | 99.1 |

As may be inferred from the table, the product loss is substantially absent.

EXAMPLE 4

The 6-month stability of a paracetamol solution prepared according to the invention and stored in infusion bags at 25° or 40° C., was tested. The solution characteristics are listed below:

| Ingredients | (% w/v) |
|---|---|
| Paracetamol | 1.0 |
| Propylene glycol | 0.8 |
| Monohydrated citric acid | 0.045 |
| Disodium hydrogen phosphate.$2H_2O$ | 0.091 |
| Sodium chloride | 0.3 |
| Injection water | to 100 ml |
| Heating time | 20 min |
| Heating temperature | 120° C. |
| Recrystallisation | no |

A first lot (stability No. 01007) having the composition described above, was produced on a semi-commercial scale (350 l) by the following method: paracetamol was added to a water/propylene glycol solution, preheated to 70° C.-95° C.

The resulting solution was added with monohydrated citric acid, disodium hydrogen phosphate.2H$_2$O, and sodium chloride. The solution was stirred for 20 min and, still hot (70° C.-90° C.), was poured into 100 ml polypropylene bags for infusion. The bags were heated to 120° C. and maintained at said temperature for 20 minutes.

A second lot (stability No. 01008) having the same composition as the first one, was prepared according to the method described above.

The stability tests on the two lots were conducted according to ICH's guidelines: 25±2° C. at 60±5% RH, and 40±2° C. at 75±5% RH. Paracetamol and its main degradation product, p-aminophenol, were evaluated by HPLC. The 6-month paracetamol loss was evaluated in respect of the initial paracetamol quantity (100%). The results obtained are shown in the following table:

|  | Stability No. 01007 | | Stability No. 01008 | |
| --- | --- | --- | --- | --- |
| Temperature | 25° C. | 40° C. | 25° C. | 40° C. |
| Initial quantity | 100.2 | 100.2 | 100.4 | 100.4 |
| After 3 months | 99.8 | 100.0 | 99.8 | 100.2 |
| After 6 months | 100.1 | 100.1 | 100.1 | 100.2 |

As may be inferred from the table, there is no product loss after 3 and 6 months. The main product of degradation, p-aminophenol, is below the detection limits. The final solution is stable and reproducible.

EXAMPLE 5

The stability of a paracetamol solution stored for an extended period of time at high temperature was evaluated by the following test.

A 2,800 l lot of a 1% paracetamol solution as described above, was stored at 70° C.-95° C. for 24 hours.

The bulk product and the finished product, sterilised at 120° C. for 20 min, were poured into polypropylene bags, sampled and tested.

|  | Just prepared | | Ater 24 hrs (70-95° C.) | |
| --- | --- | --- | --- | --- |
|  | Bulk solution | Sterilised solution | Bulk solution | Sterilised solution |
| PH | 5.5 | 5.5 | 5.5 | 5.5 |
| Osmolality (mosm/kg) | — | 281 | — | 284 |

|  | Just prepared | | Ater 24 hrs (70-95° C.) | |
| --- | --- | --- | --- | --- |
|  | Bulk solution | Sterilised solution | Bulk solution | Sterilised solution |
| paracetamol (%) | 99.2 | 99.5 | 99.5 | 99.5 |
| 4-aminophenol (%) | n.d. | n.d. | n.d. | n.d. | n. d.: not determined

The solution, stored at 70°-95° C. for 24 hrs, is stable; no paracetamol degradation occurred.

The invention claimed is:

1. A process for the preparation of a packaged, ready-to-use paracetamol injectable solution, the process comprising: mixing paracetamol with water, propylene glycol as the only co-solvent, and a citrate buffer (pH from 4.5 to 6.5), heating said solution to a temperature between 70° C. and 130° C., keeping same at said temperature for 10 min at least, wherein the heating to between 70° C. and 130° C. is followed by a packaging step, and the packaging step is followed by a sterilization step.

2. The process according to claim 1, wherein paracetamol is added in such a quantity as to secure a concentration lower than or equal to 4% by weight.

3. The process according to claim 1, wherein propylene glycol is added in such a quantity as to secure a final concentration of 0.1% to 40% w/v.

4. The process according to claim 3, wherein propylene glycol is added in such a quantity as to secure a final concentration of 0.5% to 20% w/v.

5. The process according to claim 4, wherein propylene glycol is added in such a quantity as to secure a final concentration of 0.5% to 10% w/v.

6. The process according to claim 5, wherein propylene glycol is added in such a quantity as to secure a final concentration of 0.7% to 3% w/v.

7. The process according to claim 1, wherein the pH of said citrate buffer is in the range from 5 to 6.

8. The process according to claim 7, wherein said citrate buffer consists of citric acid and disodium monohydrogen phosphate.

9. The process according to claim 1, wherein said solution is filled into injection phials or bottles or perfusion bags.

10. A method to enhance the stability of paracetamol liquid pharmaceutical compositions, characterized in that paracetamol is formulated by mixing paracetamol with water, propylene glycol as the only co-solvent, and a citrate buffer (pH from 4.5 to 6.5), heating said solution to a temperature between 70° C. and 130° C., keeping same at said temperature for 10 min at least, wherein the heating to between 70° C. and 130° C. is followed by a packaging step, and the packaging step is followed by a sterilization step.

* * * * *